United States Patent [19]

Liljeström et al.

[11] Patent Number: 5,055,401

[45] Date of Patent: Oct. 8, 1991

[54] CONSTRUCTION OF NEW α-GALACTOSIDASE PRODUCING YEAST STRAINS AND THE INDUSTRIAL APPLICATION OF THESE STRAINS

[75] Inventors: Pirkko L. Liljeström, Vantaa, Finland; Roy S. Tubb, Deal, England; Matti P. Korhola, Helsinki, Finland

[73] Assignee: Alko Ltd., Helsinki, Finland

[21] Appl. No.: 36,649

[22] Filed: Apr. 10, 1987

[51] Int. Cl.$^5$ .................... C12N 15/00; C12N 9/40; C12P 19/39

[52] U.S. Cl. ............................ 435/172.3; 435/208; 435/254; 435/255; 435/256; 435/320.1; 435/100; 435/105; 435/91; 536/27; 935/27; 935/28; 935/37; 935/56; 935/69; 935/78; 935/82

[58] Field of Search ............... 435/320, 172.3, 208, 435/91, 255, 256, 100, 105; 935/28, 27, 37, 56, 69, 78, 82; 536/27

[56] References Cited

U.S. PATENT DOCUMENTS

| | | | |
|---|---|---|---|
| 4,376,167 | 3/1983 | Vitobello et al. | 435/276 |
| 4,431,737 | 2/1984 | Oliveri et al. | 435/208 |
| 4,784,949 | 11/1988 | Gelfund | 435/34 |
| 4,931,373 | 6/1990 | Kawasaki et al. | 435/172.3 |

FOREIGN PATENT DOCUMENTS 86103777 7/1986 PCT Int'l Appl. .

OTHER PUBLICATIONS

Tajima et al., *Mol and Cell Biol.*, 6(1):246-256, 1986.
Ruohola, H. et al., *FEMS Micro. Lett.* 34:179-185 (1986).
Tubb, R. S., *J. Inst. Brew.* 93:91-96 (1987).
International Biotechnologies, Inc., 1985 Catalog, pp. 4 and 240.
Wolfrom, M. L., Physical and Chemical Structures of Carbohydrates in: Symposium on Foods: Carbohydrates and Their Roles, H. W. Schultz et al., eds. (1969), AVI Publishing Co., Westport, CT.
Kielland-Brandt, M. C. et al., Chapter 13 in: Yeast Genetics, J. F. T. Spencer et al., eds., Springer-Verlay, N.Y., 1983, pp. 421-437.
Snow, R., Chapter 14 in: Yeast Genetics, J. F. T. Spencer et al., eds., Springer-Verlag, N.Y., 1983, pp. 439-459.
Meaden, P. et al., *Gene* 34:325-334 (1985).
Enevoldsen, B. S., *Carlsberg Res. Commun.* 46:37-42 (1981).
Enevoldsen, B. S., *J. Am. Soc. Brew. Chem.* 63:183-184 (1985).
Tubb, R. et al., *13th Int. Conf. Yeast Gent. Molec. Biol.* (Banff, Alberta, Canada, 1986 Yeast 2(Spec. Iss): S396 (1986).
Henderson, R. C. A. et al., *Curr. Genet.* 9:133-138 (1985).
Post-Beittenmiller, M. A. et al., *Mol. Cell. Biol.* 4:1238-1245 (1984).
Liljestrom, P. L., *Nuc. Acids Res.* 13:7257-7268 (1985).
Sumner-Smith, M. et al., *Gene* 36:333-340 (1985).
Hinnen, A. et al., *Proc. Natl. Acad. Sci. U.S.A.* 75:1929-1933 (1978).
Kew, O. M. et al., *J. Bacteriol.* 125:33-41 (1976).
Meaden, P. G. et al., *Proc. of the 20th Europ. Brewing Conv. Congress*, Helsinki, pp. 219-226, IRL Press, London (1985).

*Primary Examiner*—Robin L. Teskin
*Attorney, Agent, or Firm*—Sterne, Kessler, Goldstein & Fox

[57] ABSTRACT

The objects of this invention are new *Saccharomyces cerevisiae* yeast strains into which α-galactosidase gene (MEL+) has been transferred by using recombinant DNA methods. Baker's and distiller's yeasts producing α-galactosidase, are utilizable in the corresponding industry, because they are able to utilize the raffinose present in molasses, which results in greater yield of yeast (or ethanol) and reduction or elimination of the costs associated with biological oxygen demand (B.O.D.) in the effluent from factories. The improved ability of brewer's yeasts to produce α-galactosidase provides a sensitive method for monitoring pasteurization of beer.

The new yeast strains prepared by using recombinant DNA methods produce more α-galactosidase than naturally occurring α-galactosidase producing yeast strains.

Also methods for marking yeast strains and for producing stable transformants of yeasts are presented.

33 Claims, 10 Drawing Sheets

FIGURE 8
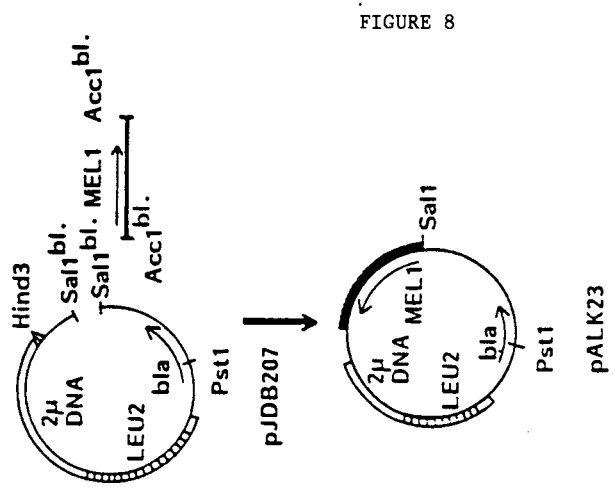
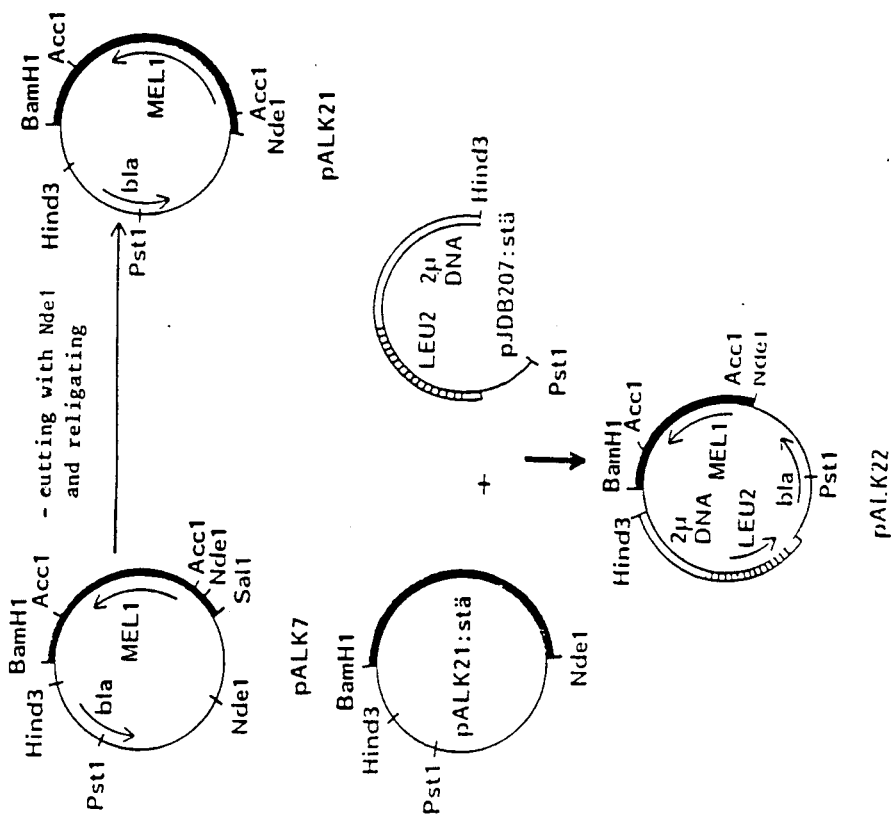

CONSTRUCTION OF NEW α-GALACTOSIDASE PRODUCING YEAST STRAINS AND THE INDUSTRIAL APPLICATION OF THESE STRAINS

BACKGROUND OF THE INVENTION

1. Field of Invention

α-Galactosidase (E.C 1.2.1.22) is an enzyme able to hydrolyse melibiose to galactose and glucose. Some yeast species (*Saccharomyces cerevisiae* var. *oleaceus*, *Saccharomyces cerevisiae* var. *oleaginosus*, *S. cerevisiae* var. *uvarum* and *Saccharomyces cerevisiae* var. *carlbergensis*) are able to produce this enzyme naturally, but industrially used baker's and distiller's yeast strains (which belong to *S. cerevisiae*) do not produce this enzyme. This results in incomplete use of raffinose of molasses, which is widely used as a substrate for the production of baker's and distiller's yeast and sometimes used for alcohol production.

This invention comprises the construction of new baker's and distiller's yeast strains, which produce α-galactosidase. This invention comprises also the construction of new brewer's yeast strains able to produce α-galactosidase, which gives an improved method to monitor the pasteurization of beer. Inserting an α-galactosidase gene in one's baker's, distiller's or brewer's yeast provides a method of marking one's own strains or e.g. the beer produced.

2. Brief Description of the Background

Baker's and distiller's yeast

Molasses is widely used as a substrate for the production of baker's or distiller's yeast and in some countries for the production of ethanol by yeast fermentation. A typical analysis of commercially available molasses is shown in Table 1.

TABLE 1

| Analysis of commercially available molasses. | | |
|---|---|---|
| | Average value | Range of values |
| Dry weight | 80,9 | 72,15–88,34 |
| Sucrose, % of d.w. | 60,0 | 55,2–67,1 |
| Raffinose, % of d.w. | 1,55 | 0,00–4,20 |
| Invert sugar, % of d.w. | 0,41 | 0,00–3,41 |

Sucrose is the major carbohydrate present, which is metabolized by yeast via invertase-catalysed hydrolysis to glucose and fructose (FIG. 9). Also present in measurable quantities (ca. 1%) is raffinose. Since baking and distilling strains of yeast secrete invertase, they are able to hydrolyse raffinose to melibiose and fructose. However, most baking or distilling strains (being classified as *Saccharomyces cerevisiae* according to van der Walt, 1970 The Yeasts, 555–718) do not secrete α-galactosidase and therefore are unable to hydrolyse melibiose to galactose and glucose. Such strains are described as being able to utilize ⅓ raffinose whereas strains which produce both invertase and α-galactosidase can utilize raffinose completely. The construction of Mel+ baking or distilling strains by transfer of a MEL gene conferring production of an extracellular α-galactosidase is therefore attractive so that the carbohydrate present in molasses can be utilized more completely. This results in:

(i) A greater yield of yeast or ethanol from molasses (ii) Reduction or elimination of the cost associated with the melibiose contribution to biological oxygen demand (B.O.D.) in the effluent from factories using molasses as a fermentation substrate.

Baker's yeast is a widely distributed product. Consequently, yeast manufacturers find it very difficult to protect or retain their own strains which are, in the natural course of things, available to competitors. This has led to an uncontrolled exchange of strains and this inhibits any one manufacturer from committing substantial effort to strain improvement. According to this invention the MEL1 gene has been inserted into a LEU2 gene in a recipient baker's yeast strain. This provides the recipient strain with a unique fragment of DNA which can be recognized using the cloned MEL1 and/or LEU2 gene as a molecular probe(s). This provides a method of "marking" a production strain so that its use by one's competitors can be readily detected and thereby prevented.

Brewer's yeast

Brewing ale strains (*Saccharomyces cerevisiae*) do not produce α-galactosidase, whereas brewing lager strains (*S. cerevisiae* var. *uvarum* or *carlsbergensis*) have this ability (i.e. they are Mel+). The presence of (α-galactosidase has been demonstrated in lager beers and measurement of melibiase activity has been proposed as a method of determining the number of pasteurization units a beer has received (Enevoldsen, 1981, Carlsberg. Res. Commun. 46, 37–42; Enevoldsen, 1985, J. Am. Soc. Brew. Chemists, 63, 183–184). Standardization of pasteurization treatments is important in controlling beer quality. However, the melibiase inactivation method is not generally applicable at present to quantifying the treatment received because of low or (with ale strains) zero amounts of enzyme produced. Introduction of a cloned MEL gene into brewing strains by recombinant DNA technology, therefore offers the possibility of extending the method of Enevoldsen to beers other than lagers and, by increasing the amount of α-galactosidase produced, improving the sensitivity and reproducibility of the method. Further, since a significant proportion of α-galactosidase remains in the yeast cell wall, surplus yeast from brewery fermentations using strains with high α-galactosidase activity, will be enriched with this enzyme. Such enriched yeast could be used for hydrolysing α-galactosides in animal feed materials and therefore should have enhanced value as a feed ingredient.

Transfer of the α-galactosidase encoding gene to brewing strains makes it possible to "mark" ones own brewer's yeast strains as described in connection of baker's yeast, but it makes it also possible to "mark" the produced beer. According to this invention α-galactosidase can be detected straight from beer, which is a simple way to show that the α-galactosidase producing strain has been used in beer production. In this respect, the Mel+ characteristic of brewing lager strains is encoded by a gene which differs substantially from MEL1 (i.e. it does not hybridize in DNA-DNA hybridizations (Tubb, R., Liljeström, P., Torkkeli, T. & Korhola, M. (1986) 13th International Conference on Yeast Genetics and Molecular Biology, Banff, Alberta, Canada 1986, Yeast 2 (Spec. Iss.) 1986 S396). Therefore even a lager beer can be marked by transfer of the MEL1 gene into a lager strain of yeast if one has an immunological method for detecting the MEL1 α-galactosidase.

Yeast strains for effective α-galactosidase production

α-Galactosidase is a useful enzyme with application in (for example): (i) hydrolysis of raffinose to aid crystallization of sucrose during refining of sugar beet (ref.

Obara, J. & Hashimoto, S. 1976, Sugar Technol. Rev. 4: 209–258), (ii) reducing levels of higher galactosides (stachyose, verbascose) in feed/food materials such as soya meal or soya milk-substitute (Schuler, R., Mudgett, R. E. & Mahoney, R. R. 1985. Enzyme Microb. Technol. 7: 207–211). High levels of these galactosides cause excessive flatulence when present in the diet and this is a major limitation to the exploitation of food materials derived from seed legumes.

The use of Saccharomyces strains to produce a commercial α-galactosidase has been considered previously (Vitobello, V., Branduzzi, P. & Cimini, N., U.S. Pat. No. 4,376,167; Olivieri, R., Panselli, P., Fascetti, E. & Ciuffolotti, P., U.S. Pat. No. 4,431,737). For use in sugar processing, enzyme preparations are required to be free from invertase. For this reason, the use of naturally occurring Mel+Suc− strains of S. cerevisiae var. oleaceus or S. cerevisiae var. oleaginosus has been proposed.

According to this invention new yeast strains have been constructed, which produce levels of α-galactosidase 2 to 8-fold greater than those produced by naturally occurring strains. α-Galactosidase could be produced also as a byproduct of baker's or distiller's yeast production.

A method for introducing recombinant DNA into industrial yeast strains and for obtaining stable transformants Obtaining transformants of yeast strains requires a good method of selecting out those yeast cells which have taken up the DNA of interest. In fundamental studies with *Saccharomyces cerevisiae*, this is usually accomplished by including within the recombinant DNA, a selectable marker gene (e.g. LFU2, HIS3, URA3, TRP1) which complements a corresponding auxotrophic mutation in the chosen recipient. After treatment with DNA, protoplasts or cells are plated on (or in) a medium which does not provide the auxotrophic requirement of the recipient strain. Therefore, only transformants are able to grow.

Brewing, baking, distilling or wine yeasts are usually wild type (i.e. they do not have any auxotrophic requirements) and it is neither practicable nor desirable to introduce auxotrophic mutations into these strains. Therefore, transformation of industrial yeasts requires the use of dominant marker genes which are selectable against a wild-type polyploid background. For example, genes conferring resistance, to the aminoglycoside antibiotic, G418 (Webster, T. D. & Dickson, R. C. (1983). Gene 26: 243–252) or to copper ions (Henderson, R. C. A., Cox, B. S. and Tubb, R. (1985) Current Genetics 9: 133–138) have been used. Another possibility is the use of a gene conferring the ability to grow on a novel substrate. We show that the yeast MEL1 gene can be introduced into industrial yeast strains by selecting transformants on a medium containing melibiose as the sole carbon source. The use of a medium containing the chromogenic substrate, x-α-galactosidase (5-bromo-4-chloro-3-indolyl-α-D- galactoside also called x-α-gal) provides confirmation that putative Mel+ transformants produce α-galactosidase. X-α-galactoside can be incorporated into the medium used initially for obtaining transformants and/or during subsequent confirmatory tests. Mel+ colonies turn blue-green on media containing x-α-galactoside and this provides a convenient way of identifying those transformants which retain the transferred DNA in a stable way. (Unstable transformants segregate white colonies on media containing x-α-galactoside). Therefore since transfer of a MEL gene into yeast strains is readily selected and presence of the gene can be readily scored using x-α-galactoside, a MEL gene provides a marker gene of wide applicability in recombinant DNA technology.

x-α-galactoside substrate can be used also for the detection of α-galactosidase from beer and for differentiating ale Mel− from lager Mel+ strains of yeast (Tubb, R. and Liljestrom, P. (1986) I. Inst. Brew. 92:588–590).

The new yeast strains constructed according to this invention M12E-2, M20E-1 and N12E-1 have been deposited on Mar. 27, 1986 to the National Collection of Yeast Cultures. The deposit numbers being NCYC 1567, NCYC 1568 and NCYC 1569, respectively.

This invention is illustrated by the following drawings and examples.

BRIEF DESCRIPTION OF THE DRAWINGS

FIG. 8. Construction the plasmids pALK22 and pALK23

SUMMARY OF THE INVENTION

Figure 1:
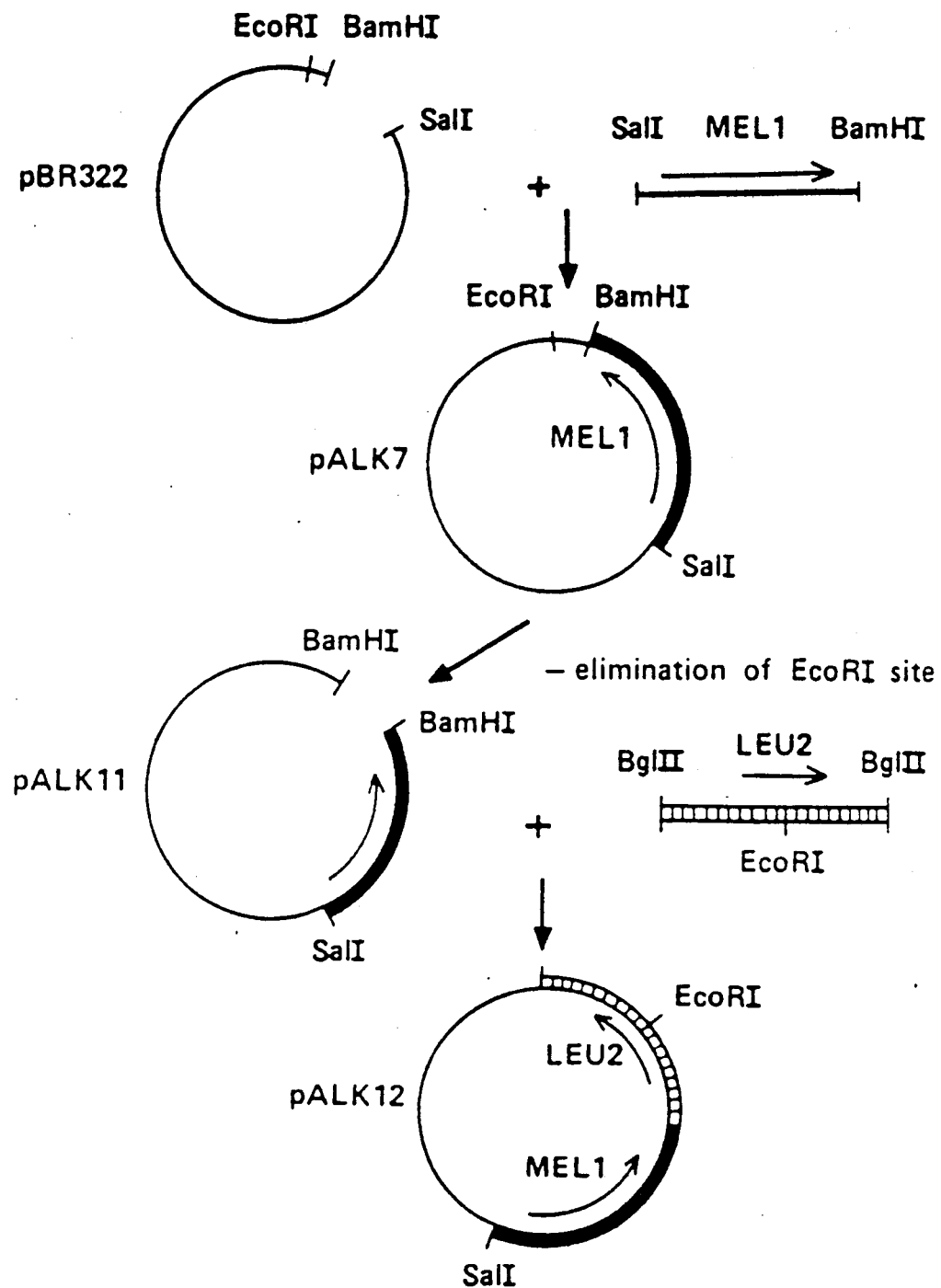
FIG. 1. Construction of the plasmid pALK12

This invention comprises the construction of new α-galactosidase producing yeast strains and the industrial application of these strains:

The construction of Mel+ (α-galactosidase-producing) baker's or distillers' yeast strains which can utilize the raffinose present in molasses, a widely used substrate for commercial yeast production, and for alcohol production.

The construction of brewer's yeast strains with enhanced capacity to produce α-galactosidase. This provides a sensitive method for monitoring pasteurization of beer and increases the value of surplus brewer's yeast as a feed supplement.

Construction of yeast strains yielding high levels of α-galactosidase for use in enzyme production. Gene transfer to Suc-(invertase negative) strains enables enzyme preparations to be produced which are not contaminated with invertase activity. This invention also comprises the novel yeast strains themselves, as well as the industrial use of these strains. According to this invention has been developed:

A method for "marking" a commercial baker's yeast or brewer's yeast, or the beer produced therewith, so that they can be unambiguously identified, thereby protecting against use of a successful strain by one's competitors.

Method for introducing recombinant DNA into industrial yeast strains and for obtaining stable transformants.

EXAMPLE 1

Construction of a gene encoding a baker's yeast strain containing α-galactosidase (M12E-2)

A genomic library of Saccharomyces cerevisiae var. uvarum strain ATCC9080 carrying the MEL1 gene was constructed in E. coli DH-1. (F-, end A1, hsdR17, SupE44, thi-1, recA1, gyrA96, relA1) as described by Ruohola, H. Liljeström, P., Torkkeli, T., Kopu, H., Lehtinen P., Kalkkinen, N. and Korhola, M. (1986) FEMS Microbiology Letters 34:179-185. Total genomic DNA was partially digested with Sau3A and ligated into the BamHI cut shuttle vector YEp13 (Broach, J., Strathern, J. and Hicks, J. (1979), Gene 8: 121-133). The resulting yeast DNA library consisted of ca. 11,000 Amp$^r$ colonies and the average size of yeast DNA insert was 7.8 kb.

The MEL1 gene was isolated from this library by complementation of mell-18 mutation in P18-la. (MATa mell-18 leu 2-3, 112 trpl ura 1) (Post-Beittenmiller, M., Hamilton, R. and Hopper, J. (1984) Mol. Cell. Biol. 4: 1238-1245) obtained from J. Hopper. The original clone which conferred the ability to produce α-galactosidase activity contained a 6.5 kb insert (PALK2). By complementation analysis the MEL1 gene was localized on a 2.8 kb BamHI/SalI fragment. The complete DNA sequence of this gene has been published (Liljeström, P., (1985) Nucl. Acids Res. 13: 7257-7268, Sumner-Smith, M., Bozzato, R., Skipper, N., Davies, R. and Hopper, J. (1985) Gene 36: 333-340, and European patent Application 0208 706). The multicopy plasmid (pALK2) carrying MEL1 gene on a 6.5 kb fragment of yeast DNA in YEp13 was transformed (Hinnen, A., Hicks, J. and Fink, G. (1978) Proc. Natl. Acad. Sci. (USA) 75: 1929-1933) into an industrially used baker's yeast strain MK270 (MK270 ferments the following sugars: galactose, glucose, fructose, mannose, maltose, sucrose and raffinose, but not the following: lactose, melibiose and inuline. The strain assimilates the following sugars: trehalose, α-methyl-D-glucoside, glyserol, furanose and meletsitose, but not the following: inuline, sellobiose and D-gluconate).

The MEL1 gene was used as a dominant selectable marker and transformants were selected on minimal melibiose plates. Transformation frequency was 60-80 transformants/μg of DNA. When these transformants were grown on nonselective melibiose fermentation indicator plates, the Mel+ phenotype was found to be unstable. Only 20-30% of the cells in a Mel+ colony were Mel+, i.e. harboring the plasmid pALK2. Mel+ transformants can be verified by the production of a non-diffusible blue dye on agar medium containing X-α-Gal. This same test was also applied to determining whether or not transformants were stable.

To obtain more stable transformants, pALK12 was constructed (FIG. 1) and integrated into chromosomal DNA of MK270. The MEL1 gene containing the 2.8 kb Sal1-BamH1 fragment was isolated from pALK2 and ligated between the Sal1 and BamH1 sites of pBR322. The resulting plasmid, pALK7 contained a unique recognition site for restriction endonuclease EcoR1. This site was destroyed by cutting the plasmid with EcoR1, filling in the sticky ends and religating. This plasmid was called pALK11. The LEU2 gene containing 2.8 kb Bgl2-Bgl2 fragment was isolated from YEp13 and ligated to the unique BamH1 site of pALK11.

The plasmid pALK12 carries the yeast LEU2 gene, which was used as a homologous sequence for recombination between the plasmid pALK12 and MK270 genome. The integration of pALK12 was directed to the LEU2 locus by linearization of the plasmid with EcoRI, which cuts in the middle of the LEU2 gene. Transformants were again selected on minimal melibiose plates. Stability of the Mel+ phenotype of these transformants was examined and 4 out of 12 were found to show 100% stability (i.e. no Mel− colonies were observed) under the test conditions. One of these, named M12E-2 was examined further.

Figure 2:
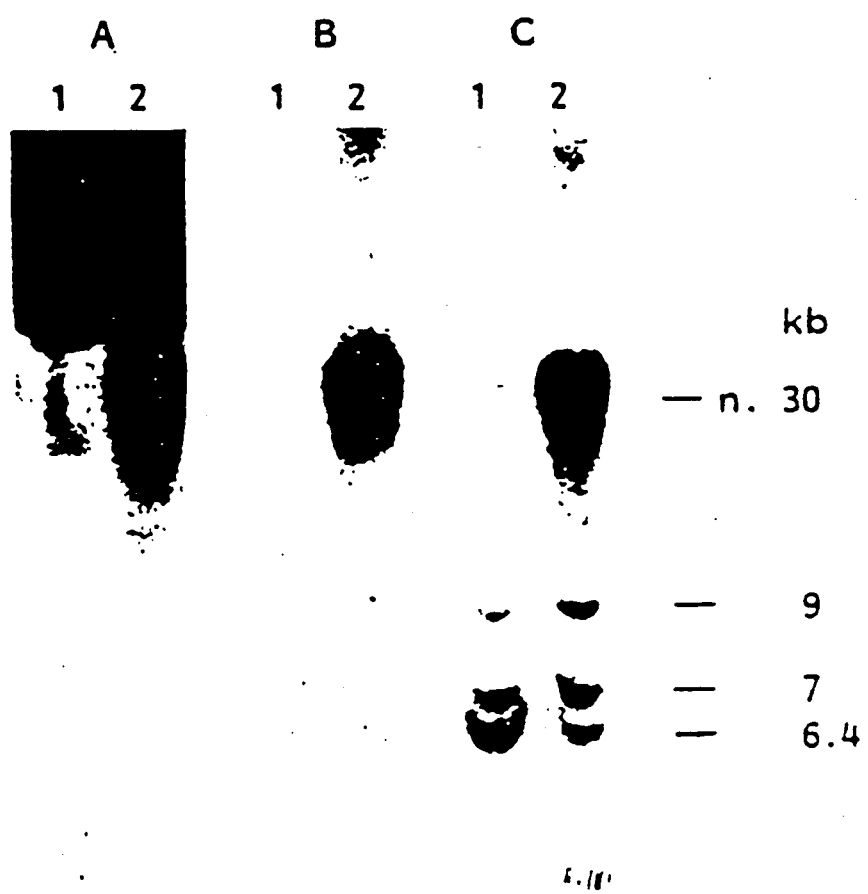
FIG. 2. Southern blot of MK270 and M12E-2 by using as a probe A) pBR 322-DNA, B) MEL1-DNA and C) LEU2-DNA. Lane 1 is DNA of MK270 and lane 2 is DNA of M12E-2.

Integration of the plasmid pALK12 in M12E-2 was confirmed by a Southern blot experiment (FIG. 2). Chromosomal DNA isolated from MK270 and M12E-2 was digested with BglII, a restriction enzyme which doesn't cut within pALK12 sequences. Southern blot hybridization was performed as described in Maniatis, T., Fritsch, E. and Sambrook, J. (1982). Molecular cloning: A laboratory manual. Cold Spring Harbour Laboratory, USA.

No homology to MEL1-specific or pBR322-specific probes was found in the original bakers' yeast MK270. But as expected a new band hybridizing to MEL1-specific, pPR322 specific and LEU2-specific probes was found in M12E-2. The LEU2-specific probe recognized three bands in MK270, which is probably due to polymorphism in the BglII recognition sites in the polyploid MK270. The same bands were still present in M12E-2 indicating that the integration event had not taken place into the LEU2 locus or more likely that integration had not occurred into all homologues of chromosome III in the polyploid MK270. It is highly likely that the integration has occurred at a LEU2 locus because it has been shown that cutting the plasmid with a restriction endonuclease which recognizes a single site within a yeast gene on that plasmid (LEU2 on pALK12) increases the transformation efficiency as well as directs the integration into that gene.

EXAMPLE 2

Construction of a baker's yeast strain containing gene encoding α-galactosidase without incorporating bacterial plasmid DNA (M20E-1)

Figure 3:
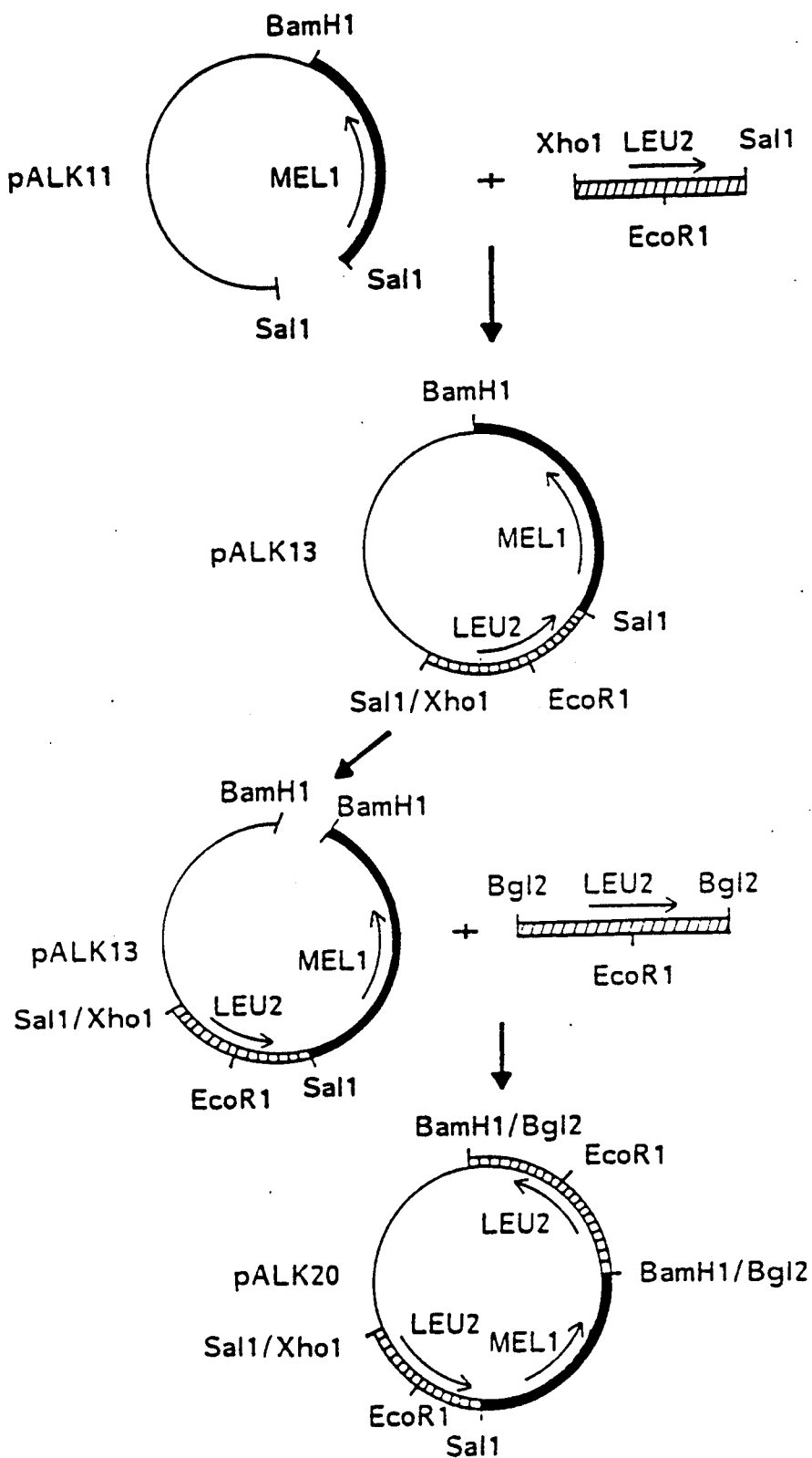
FIG. 3. Construction of the plasmid pALK20

DNA integrated to the yeast chromosome in M12E-2 transformant contains sequences from bacterial plasmid pBR322. It is desirable to construct baker's yeast strains which don't contain DNA of bacterial origin. To join MEL gene into a yeast chromosome without pBR322 sequences, a new plasmid pALK20 (FIG. 3) was constructed. The LEU2 gene containing 2.3 kb Xhol-Sal1 fragment was isolated from YEp13 and ligated to the unique Sal1 site of PALK11. The resulting plasmid pALK13 was cut with BamH1 and the LEU2 gene from YEp13 as a 2.8 kb Bgl2 fragment was ligated to the BamH1 site.

Integration of MEL1 gene to the yeast (MK270) chromosome was carried out by using EcoR1 fragment from pALK20, which consists solely of yeast DNA (yeast LEU2 and MEL1 genes). Again stable Mel+ transformants were obtained and one of these, named M20E-1 was examined further.

EXAMPLE 3

Construction of a baker's yeast strain containing gene encoding α-galactosidase in an autonomously replicating plasmid (pALK52/MK270)

A new yeast strain containing the α-galactosidase encoding gene but not any pBR sequences was constructed also by ligating the MEL1 gene to an autonomously replicating plasmid.

Figure 4:
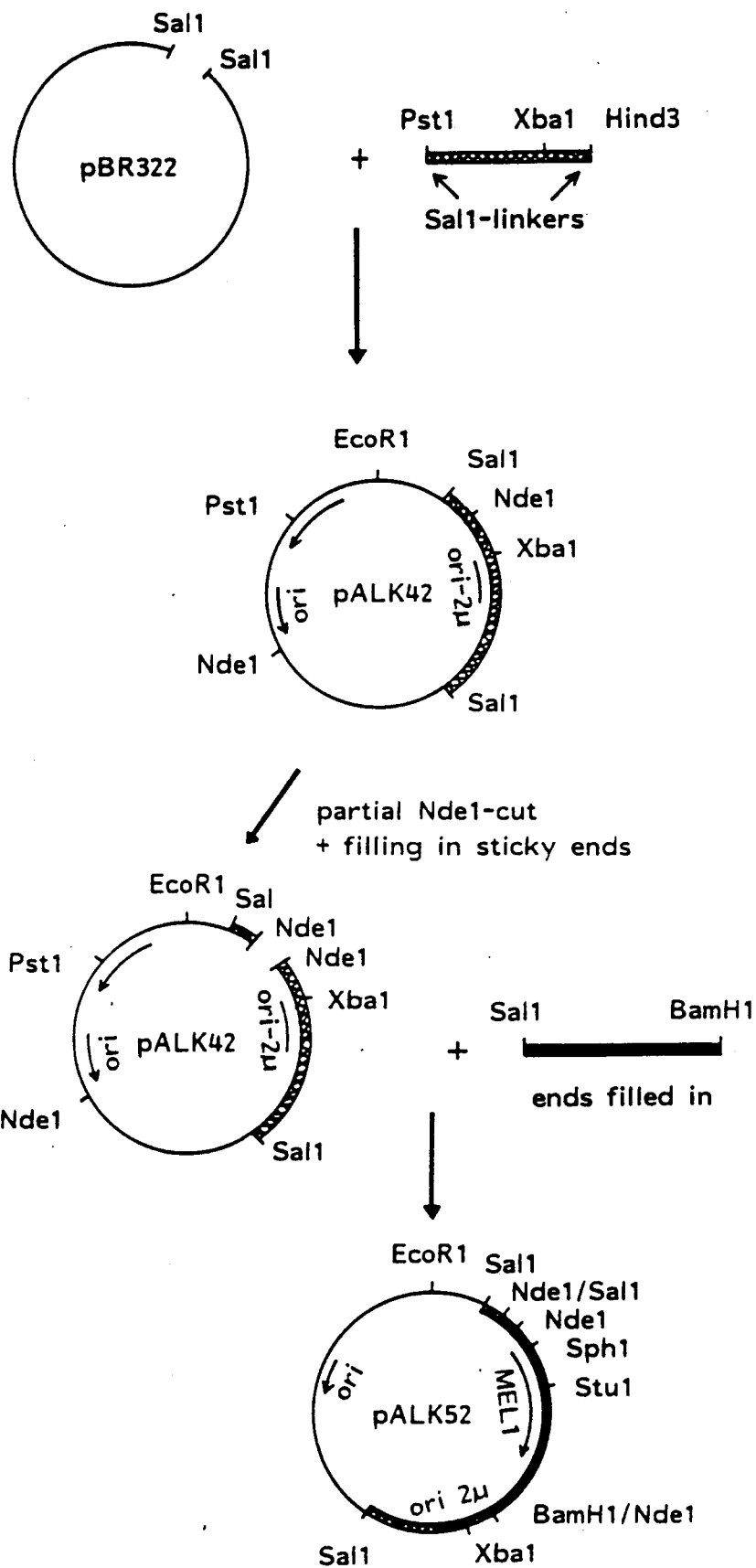
FIG. 4. Construction of the plasmid pALK52.

The plasmid pALK52 (FIG. 4) was constructed in the following way. The 2μ origin of replication containing HindIII-PstI fragment was isolated from YEp13. Using SalI-linkers this fragment was ligated into the SalI-site of pBR322. The resulting plasmid was called pALK42. The 2.8 kb SalI-BamHI fragment containing the MEL1-gene was then ligated into the NdeI-site within the 2μ fragment in plasmid pALK42. This plasmid was called pALK52. The 4.7 kb fragment of pALK52 containing the MEL1-gene and the 2μ origin of replication was isolated and ligated into a circle, which was transformed into MK270 using the MEL1-gene as selectable marker. One of the transformants pALK52/MK270, showed a stability of more than 99.9%/generation.

EXAMPLE 4

Ability of Mel+ baker's yeast strains (M12E-2 and M20E-1) to utilize raffinose of molasses Mel+ derivatives (M12E-2 and M20E-1) of baker's yeast (MK270) were tested for their ability to utilize raffinose in molasses. The conditions used were chosen to mimic commercial baker's yeast production.

Figure 5:
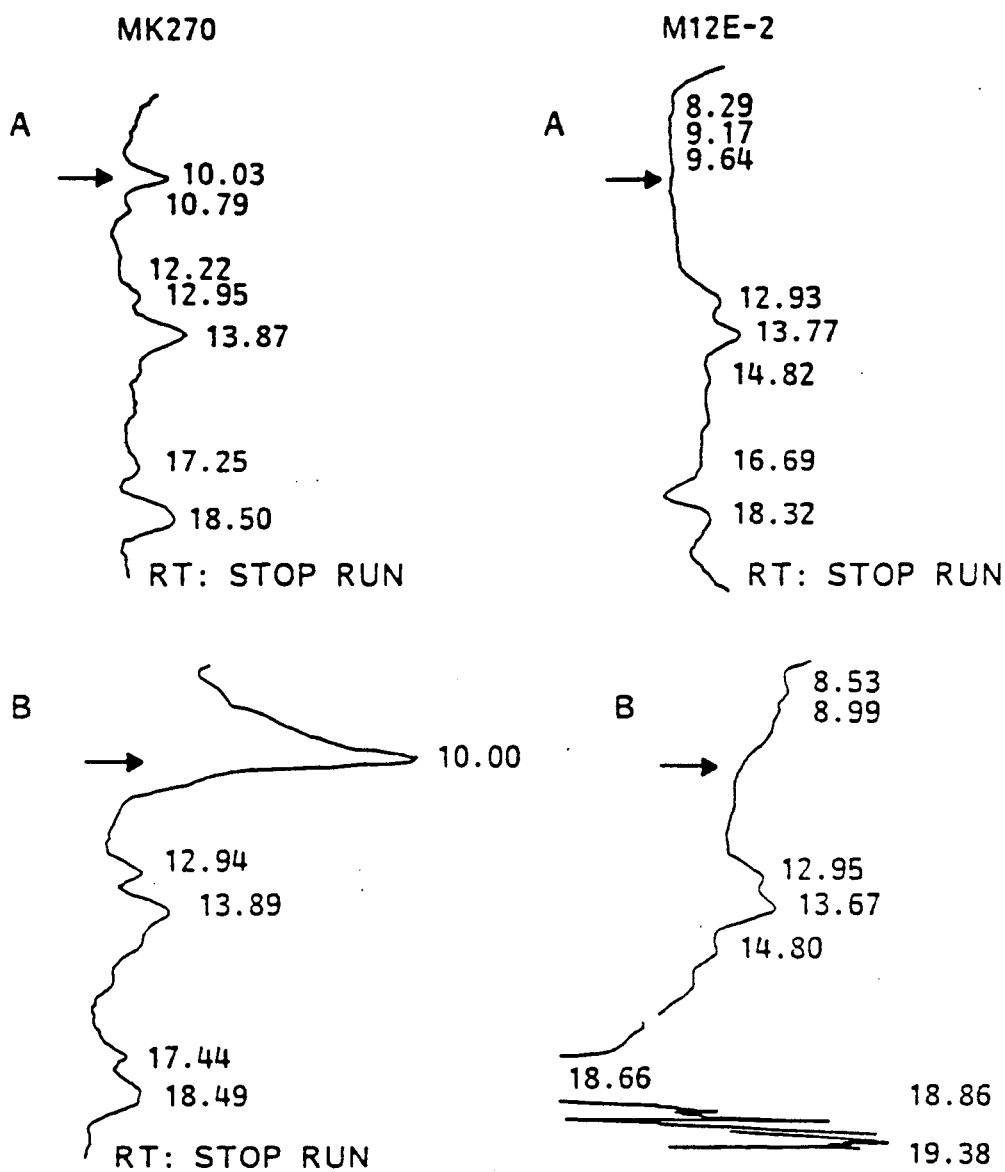
FIG. 5. Accumulation of melibiose during baker's yeast growth measured by HPLC after A) 10 h B) 16 h growth period. The arrow points to the meribiose peak.

Starter cultures of strains MK270, M12E-2 and M20E-1 were grown anaerobically in minimal galactose or minimal molasses medium. 10 g of yeast from these cultures were then inoculated in 1.8 l of water. Molasses medium contained per liter: 14.55 g of $(NH_4)_2SO_4$, 2.43 g of $NH_4H_2PO_4$, 0.61 g of $MgCl_2.6H_2O$, 0.12 mg of biotine and molasses corresponding to 5% sugar. Molasses medium was fed in gradually such that about 700 ml was used during a 16h growth period. As is shown in FIG. 5, melibiose accumulates when strain MK270 is grown on molasses, indicating that the α-galactosidic bond in raffinose is not hydrolyzed. The amount of melibiose formed (0.07%) indicates that the raffinose present is totally converted to fructose and melibiose. Therefore absence of melibiose formation during growth on molasses would indicate that raffinose is completely degraded to utilizable sugars (fructose, glucose and galactose). It can be seen that when M12E-2 was used no melibiose could be detected (FIG. 5). The same was true for M20E-1 (data not shown). The α-galactosidase activity produced by M12E-2 grown on molasses is given in Table 2. In this case, the inoculum was grown on galactose which is known to be an inducer of the synthesis of α-galactosidase (Kew, O. and Douglas, H. (1976) J. Bacteriol. 125: 33–41). However, total α-galactosidase activity increases during growth on molasses, indicating the continued production of α-galactosidase. When molasses was used for growth of the inoculum, again no melibiose accumulated indicating that sufficient α-galactosidase to fully hydrolyze raffinose is also produced under these conditions.

TABLE 2

| | α-Galactosidase production in molasses | | |
|---|---|---|---|
| Strain | Time of growth (h) | Total activity ($U_B$) | Activity in medium ($U_B$) |
| M12E-2 | 10 | 2200 | 430 |
| | 16 | 3380 | 530 |
| MK270 | 10 | 0 | 0 |
| | 16 | 0 | 0 |

Figure 6:
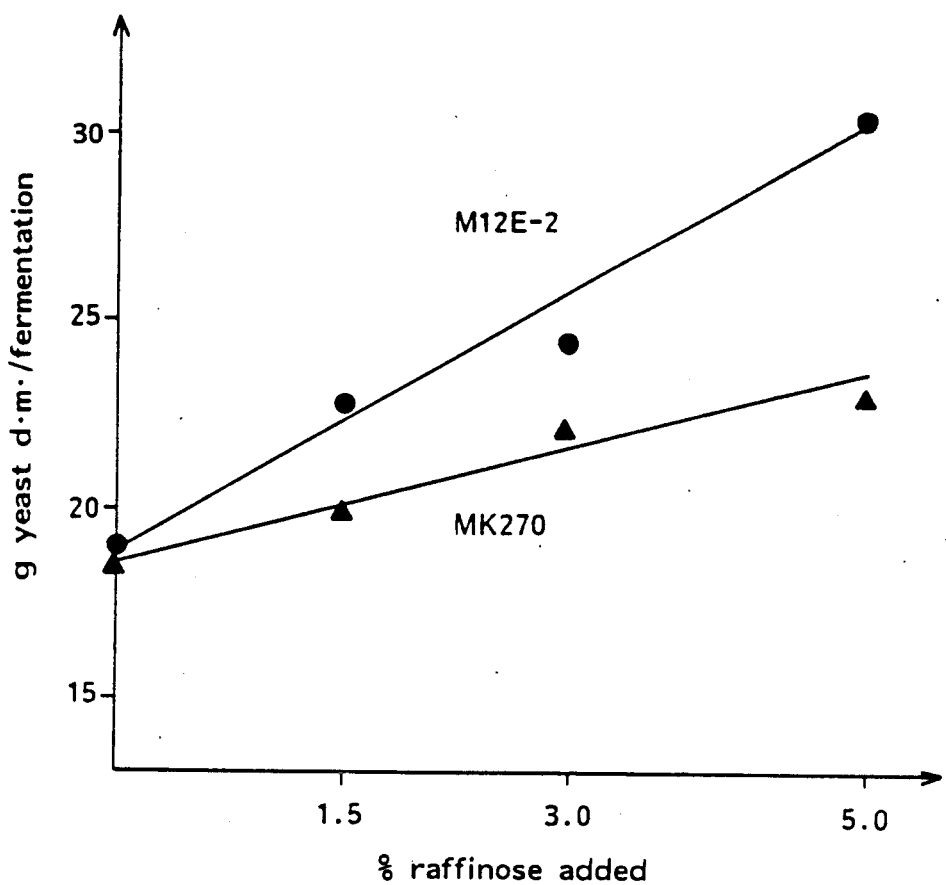
FIG. 6. A greater yield of yeast due to additional raffinose

We have shown that melibiose from raffinose is used for yeast growth in the following way. Different amounts of raffinose were added to the above described fermentation medium and the fermentation was carried out as before. As is shown in FIG. 6 considerably more biomass was produced by M12E-2 when compared with the biomass yield of MK270 in the same conditions. As expected also the biomass yield of MK270 is increased with increasing amounts of raffinose. This is due to utilization of fructose from raffinose. M12E-2 can utilize also melibiose from raffinose and thus the biomass yield is even higher.

EXAMPLE 5

Distiller's yeast strains expressing α-galactosidase gene

Since baker's yeast strains are sometimes also used in distilling, strains such as M12E-2 and M20E-1 could also be used in fermentations of molasses to provide greater utilization of carbohydrate and therefore, an increase in ethanol yield. Alternatively the MEL gene could be introduced, by the means described into specialized distillery yeasts such as the commercially available strain DCL"M", which has been shown to be amenable to genetic manipulation using recombinant DNA (Bussey, H. and Meaden, P. (1985) Current Genetics 9: 285–291). The ability of M12E-2 and M20E-1 to produce α-galactosidase is also compared under standard conditions with other strains in Table 3 (Example 6).

EXAMPLE 6

Construction of brewer's yeast strains expressing α-galactosidase gene

In a further experiment, the MEL1 gene has been introduced into a brewing ale strain NCYC 1245 using pALK2 (nonintegrating) and by integrative transformation (pALK12). A stable Mel+ transformant (N12E-1) obtained by integrative transformation is shown in Table 3 to have a much greater ability to produce α-galactosidase than a brewing lager strain (NCYC 1324) (which is naturally Mel+). The comparatively low levels produced by brewing lager strains can also be deduced from the published data of Enevoldsen (Enevoldsen (1981) Carlberg. Res. Commun. 46: 37–42; Enevoldsen (1985) J. Am. Soc. Brew. Chemists 63: 183–184). It can be seen therefore, that although brewing lager strains are already Mel+, it would be useful to consider enhancing their ability to produce α-galactosidase by use of a cloned MEL gene. In this case however, transfer of a MEL gene by direct selection of MEL+ transformants as described here is not possible. An alternative strategy is to use the yeast CUP1 (conferring copper resistance) as a means to obtain transformants. The use of the CUP1 gene as a selection system for introduction of a DEX gene into a brewing lager strain has been described by Meaden, P. and Tubb, R. (1985) In: Proceedings of the 20th European Brewery Convention Congress, Helsinki pp. 219–226. IRL Press, London.

TABLE 3

Total induced α-galactosidase activities in different strains

| Strain | α-galactosidase activity ($U_A$) | | | % of total activity in M12E-2 |
|---|---|---|---|---|
| | Total | % of total | | |
| | | Cellbound | Medium | |
| ATCC 9080 | 184 | 60% | 40% | 14,4% |
| M12E-2 | 1279 | 74% | 26% | 100% |
| M20E-1 | 113 | 72% | 28% | 8,8% |
| pALK52/MK270 | 970 | not done | not done | 76% |
| pALK4/MK270 | 920 | not done | not done | 72% |
| NRRLY12056 | 597 | 86% | 14% | 46,7% |
| NRRLY12057 | 684 | 72% | 28% | 53,5% |
| N12E-1 | 169 | 55% | 45% | 13,2% |
| NCYC1324 | 8 | 100% | not detectable | 0,6% |
| 1453-3A | 549 | 67% | 33% | 42,9% |

EXAMPLE 7

A new method for "marking" yeast or bacterium strains:

The strains constructed in Example 1 can be easily recognized by a Southern blot. This is demonstrated in FIG. 2 using the strain M12E-2. A new fragment of DNA, which is recognizable with a MEL1, LEU2 and-/or pBR322 probe is seen in M12E-2 DNA but not in MK270 DNA. The presence of this fragment distinguishes M12E-2 from any natural S. cerevisiae strain. Similarly, all other strains constructed in Example 1 are marked with a novel DNA fragment recognizable with MEL1 and/or LEU2 probes. In a similar way any yeast strain could be marked using the MEL1 gene. This includes strains that already carry a MEL gene, if the MEL1 gene is directed to a new location on a chromosome (e.g. to LEU2 locus as in Example 1). Integration to a new location leads to a new restriction fragment recognizable in Southern blot.

The MEL1 gene can also be used to mark strains of bacteria, when a piece of bacterial DNA is provided on the plasmid to allow homologous recombination between the recipient chromosome and the plasmid to be integrated.

EXAMPLE 8

α-Galactosidase production of new yeast strains constructed by using recombinant DNA methods The α-galactosidase encoded by the MEL1 gene hydrolyses melibiose, raffinose and stachyose and therefore most probably higher galactosides e.g. verbascose. Enzyme activities produced by M12E-2 against these different substrates are compared in Table 4. Activity against stachyose is needed when reduction of levels of higher galactosides in feed/food materials is considered.

TABLE 4

| Hydrolyzed sugar mg/h/activity unit* | |
|---|---|
| Melibiose | 50–70 |
| Raffinose | 11–30 |
| Stachyose | 6–20 |

*Activity unit = the amount of enzyme, which is able to hydrolyze 1 μmol PNPG/min in 30° C. and in pH 4.5.

*Activity unit = the amount of enzyme, which is able to hydrolyze 1 μmol PNPG/min in 30° C. and in pH 4.5.

The α-galactosidase encoded by MEL1 can hydrolyze 0.1 mg stachyose/h/$U_{PNPG}$ in 10% soya meal (T=40° C., pH 5.5, 10 $U_{PNPG}$/g soya meal).

Figure 7A:
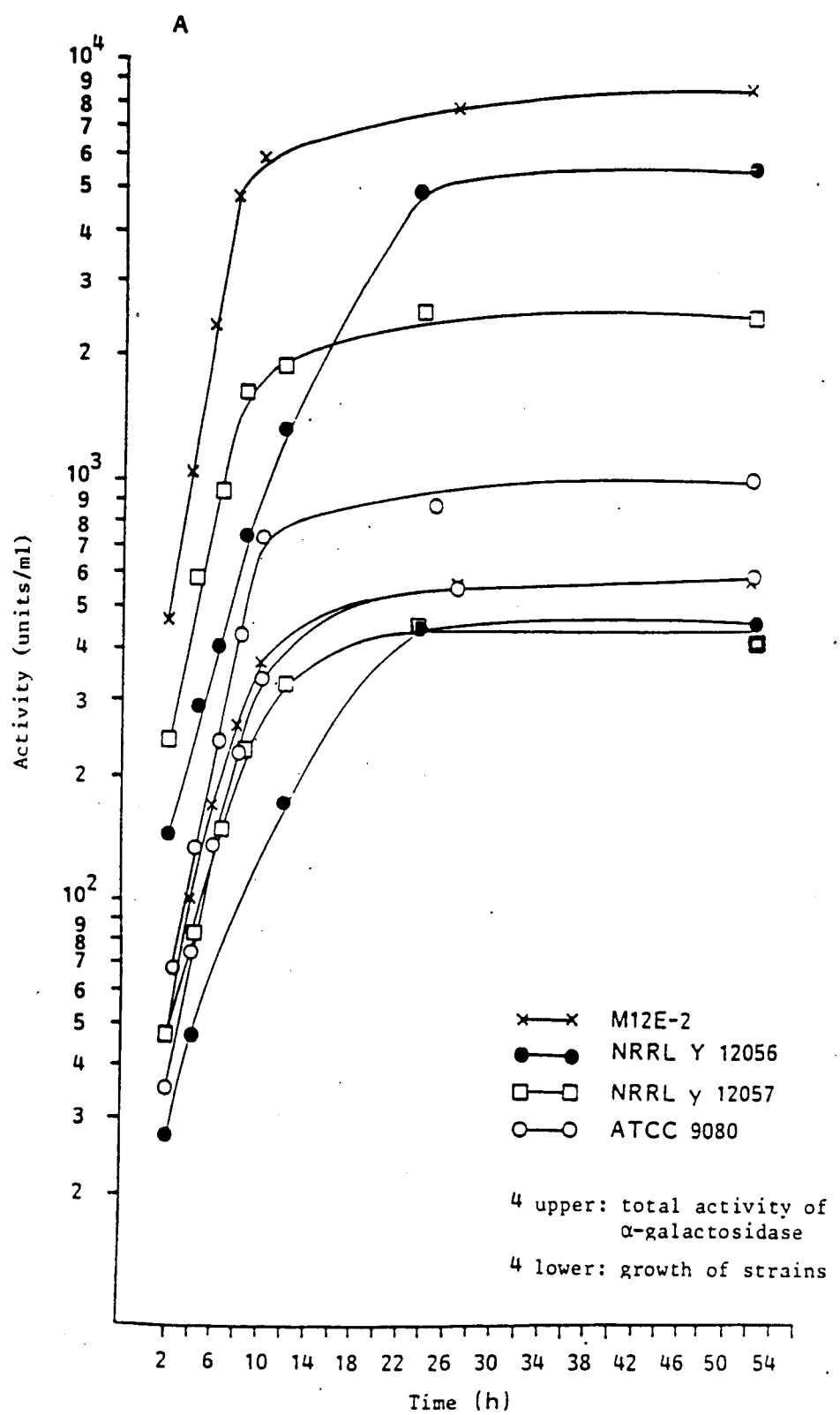
FIG. 7A. Total α-galactosidase production of different strains during growth.

FIG. 7A illustrates the kinetics of α-galactosidase production and the total amounts produced during growth in YP+gal5%+glys3%+EtOH2% of different strains. The highest amount of enzyme is produced by M12E-2 (Mel+ derivative of baker's yeast). In this case with use of recombinant DNA techniques an 8-fold increase in enzyme production has been achieved. The original strain ATCC9080 produces only $10^3$U of α-galactosidase M12E-2 produces $8 \times 10^3$U.

The higher amount of enzyme produced by M12E-2 is likely to be due to the higher copy number of the MEL1 gene in this strain. In Southern blot (FIG. 2) the new LEU2-hybridizing band is darker compared to the original ones indicating that copy number of the integrated plasmid is higher than that of the LEU2 gene. This is also supported by the large size of the new band (greater than or equal to 30kb). If only one copy of pALK12 had integrated at the LEU2 locus the expected size of the new band would be 16–19 kb.

Figure 7B:
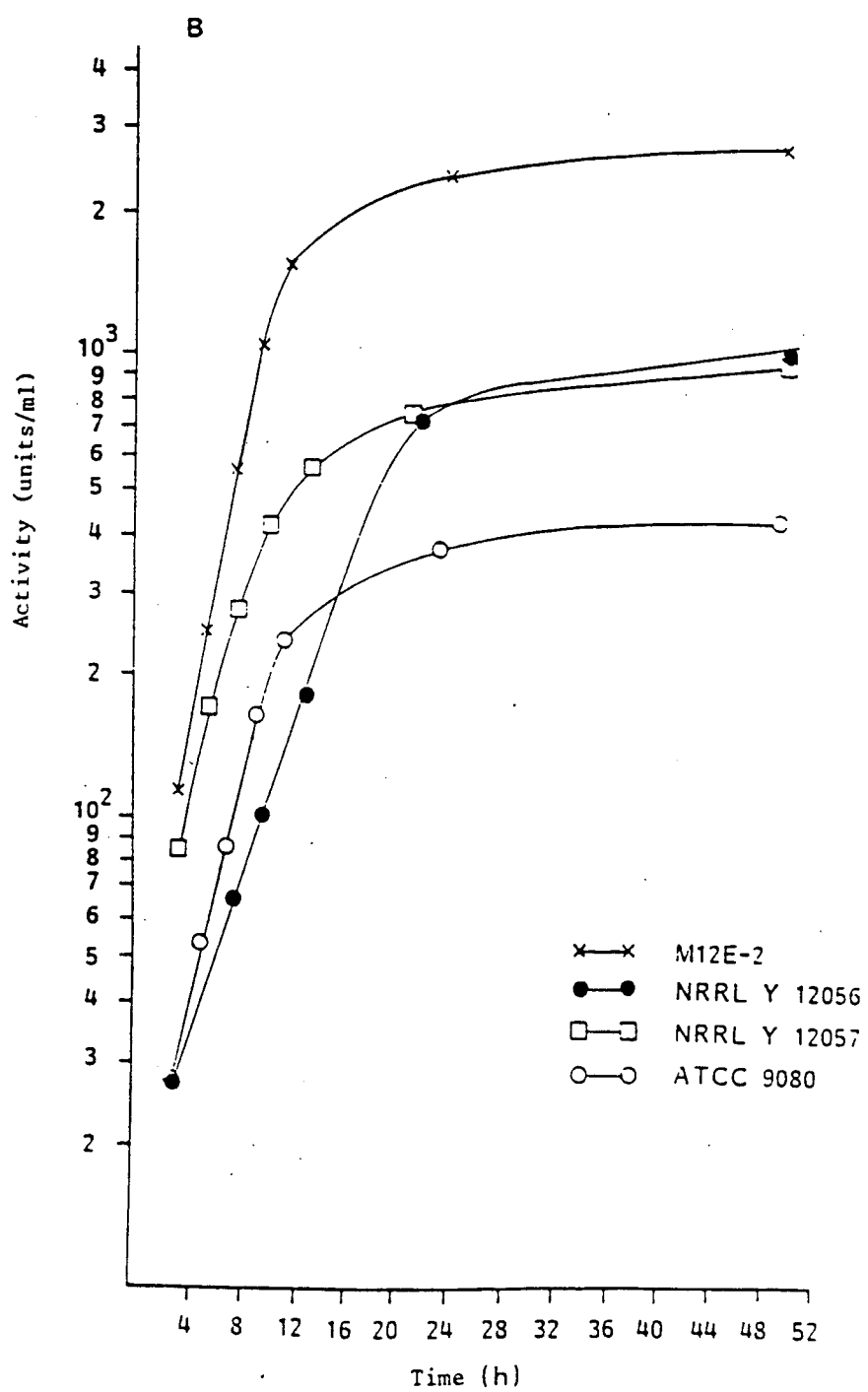
FIG. 7B. n-Galactosidase activity secreted into the growth medium from the same samples as in FIG. 7A.
Figure 9:
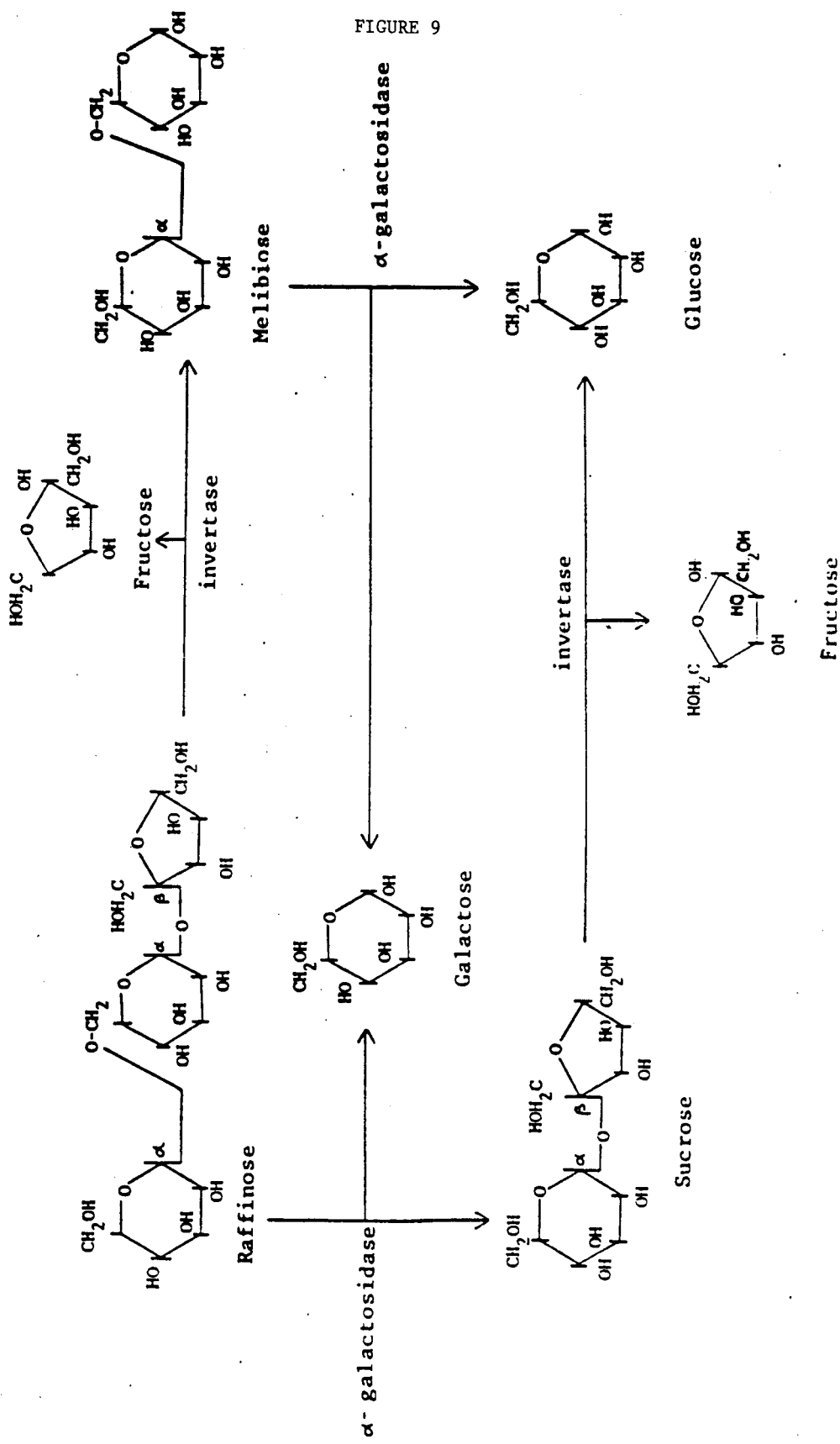
FIG. 9. Sucrose metabolism in yeast.

S. cerevisiae var. oleaceus, NRRL Y 12056 (U.S. Pat. No. 4,376,167) produces almost as much enzyme as M12E-2 but much more slowly. M12E-2 produces $5=10^3$U of α-galactosidase in 8h when for NRRL Y 12056 it takes 24 h (FIG. 7A). A second advantage of M12E-2 when compared to NRRL Y 12056 and NRRL Y 12057 (U.S. Pat. No. 4,431,737) is that it secretes 3 times more α-galactosidase in culture medium (FIG. 7B). This is important if the enzyme is to be purified from the spent medium, as might be desirable in for example, producing α-galactosidase as a by-product of baker's yeast manufacture. Addition of the strain NRRLY 12057 (U.S. Pat. No. 4,431,737) to soya bean meal has been proposed. This yeast contained 1.2·$10^5$ units of α-galactosidase activity (equals 11000 U used in U.S. Pat. No. 4,431,737) per gram of dry microbial cells. When M12E-2 was grown in a fermentor as described in Example 4, it contained 7.8-$10^5$ U per gram of yeast dry matter.

As mentioned earlier, for applications in the sugar industry preparations of α-galactosidase should be invertase free. For this purpose the MEL1 gene can be transferred into a Suc− mutant of S. cerevisiae to increase α-galactosidase production. An available S. cerevisiae Mel+ Suc− mutant 1453-3A (Suc MAL2 MEL1 his4 leu2, Yeast Genetic Stock Center, Berkeley, Calif.) produces already about the same amount of enzyme as the naturally occurring Suc− Mel+ yeasts NRRL Y 12056 and NRRL Y 12057 (Table 3). The MEL1 gene could be transferred into 1453-3A using pALK2 or pALK12 and the LEU2 gene as a selectable marker since 1453-3A is a leu2⁻ mutant. This should increase the amount of α-galactosidase produced by 1453-3A, since it has already been demonstrated above that increase in copy number of the MEL1 gene seems to increase the enzyme production as well: compare M12E-2 to M20E-1 and ATCC9080 in Table 3. Alternatively, high level production of α-galactosidase by a Suc⁻ strain could be achieved by inactivating the SUC gene(s) in a Mel⁺ strain such as M12E-2.

The yeast itself containing α-galactosidase activity in the cell wall could be used as a feed supplement as proposed above. This is attractive particularly for the utilization of surplus brewer's yeast. As is shown in Table 3 most (over 70%) of the α-galactosidase produced by the Mel⁺ transformants of baker's yeast (i.e. strains M12E-2 and M20E-1) was cell bound. In the lager strain NCYC1324 (naturally Mel⁺) all α-galactosidase activity was cell bound, but the amount of enzyme present was very low. In the Mel⁺ derivative of an ale strain (N12E-1) the amount of cell bound enzyme (55% of total) is more than 10 fold greater than that naturally present in NCYC 1324.

EXAMPLE 9

Increase in α-galactosidase production

Figure 10:
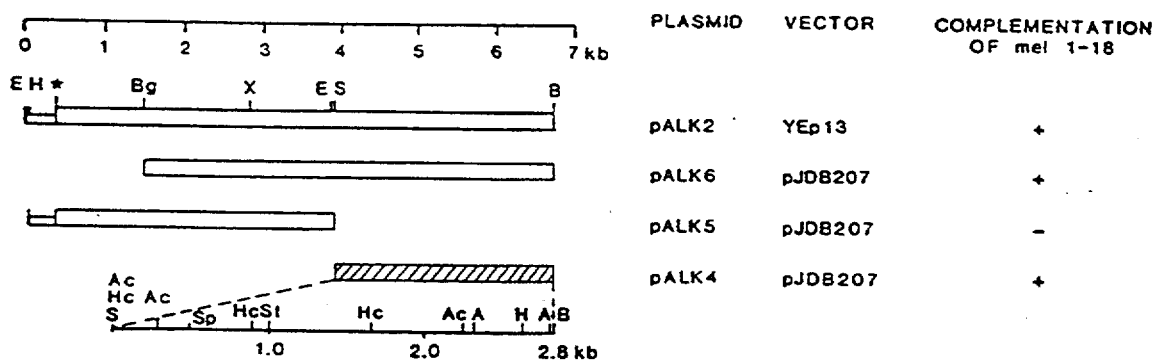
FIG. 10. Restriction map of the yeast DNA insert in plasmids pALK2 and pALK4 and complementation pattern of pALK2 subclones. Insert of the yeast DNA in pALK2, given by the open bar, is in the BamHI site of YEp13. The thin line represents vector DNA. * denotes the Sau3A-BamHI junction between the insert and the vector. Symbols for restriction enzymes are as follows: A, AvaI; Ac, AccI; B, BamHI; Bg BglII; E, EcoRI; H, HindIII; Hc, HincII; S, SalI; Sp, SphI; St, StuI; X, XhoI. The open bars below the map of plasmid pALK2 represent DNA segments of pALK2 cloned in pJDB207. More detailed restriction map of the yeast DNA insert in pALK4 is shown at the bottom.

Using recombinant DNA techniques for production of α-galactosidase producing strains can be further developed. Here we demonstrate that by deleting parts of the 5' regulatory region of the MEL1 gene the level of α-galactosidase expression in glucose medium is increased (Table 5). The wild type MEL1 gene is not transcribed in the presence of glucose (Post-Beittenmiller, M., Hamilton, R. and Hopper, J. (1984) Mol. cell. Biol. 4: 1238-1245). All the strains in Table 5 carry the MEL1 gene on a multicopy plasmid pJDB207 (Beggs, J. (1981) In: Williamson, R. (ed.) Genetic engineering 2. Academic Press, New York pp. 175-203). The plasmid pALK4 contains about 2.8 kb of the MEL1 5' region (FIG. 10 and Ruohola, H., Liljeström, P., Torkkeli, T., Kopu, H., Lehtinen, P., Kalkkinen, N. and Korhola, M. 1986) FEMS Microbiology Letters 34: 179-185), which is assumed to contain all regulatory sequences. The α-galactosidase activity (31 U, Table 5) in glucose media is probably due to the high copy number of the MEL1 gene leading to partial escape of normal glucose repression. The other two plasmids PALK22 and pALK23 contain only 243 bp and 175 bp of the MEL1 5' region, respectively. The construction of these plasmids has been done in the following way (FIG. 8). The plasmid pALK7 was cut with NdeI and religated resulting in deletion of the smaller NdeI fragment (plasmid pALK21). The larger HindIII-PstI fragment of this plasmid was then ligated with HindIII-PstI-cut pJDB207 to provide a selectable marker (LEU2) and replication origin in yeast. The resulting plasmid was called pALK22. To construct a plasmid with an even shorter MEL1 5' region the MEL1 gene containing AccI-AccI fragment from pALK7 was isolated and the sticky ends were filled in. This fragment was then ligated with Sa1I-cut pJDB207, where the sticky ends had also been filled in. The resulting plasmid was called pALK23.

As shown in Table 5 normal regulation of MEL1 expression in strains carrying these plasmids is abolished. Quite high expression occurs in the presence of glucose (148 U and 441 U); in pALK23/YF135 even 14 fold higher than pALK4/YF135. Since the vector part of these plasmids is the same there should be no significant difference in the copy number of the MEL1 gene and the higher expression of the MEL1 gene on plasmid pALK23 is likely to be due to the altered 5' region.

To increase MEL1 expression further high efficiency promoters (e.g. PGK or ADH), Dobson, M. J., et al. (1982) Nucl. Acids Res. 10:2625-2637; Ammerer, G., in, *Methods in Enzymology*, volume 101, Academic Press, New York, pp. 192-201, could be used to direct MEL1 transcription.

TABLE 5

Total α-galactosidase activities in 5' deletion strains

| Strain | Carbon Source | |
|---|---|---|
| | glc 5% | gal 5% + glys 3 + EtOH2 |
| pALK4/YF135* | 31 | 1146 |
| pALK22/YF135 | 148 | 688 |
| pALK23/YF135 | 441 | 866 |

*YF135, α, leu 2-3, 112, his 3-11, 15 (Yeast strain YF135 has been obtained from recombinant DNA Methodology Course in Ottawa in August 1982)

METHODS

Measurement of α-galactosidase levels

α-Galactosidase levels were measured essentially as described by Kew and Douglas (Kew, O. and Douglas, H. (1976) J. Bacteriol. 125: 33-41). Yeast cells were grown in appropriate medium and samples were taken and chilled on ice. When total activities were measured the culture as such was used as sample. The final reaction mixture (450 μl) contained 50 mM PNPGal (p-nitrophenyl-α-D-galactopyranoside) buffered to pH 4.0 with 31 mM citric acid and 39 mM $KH_2PO_4$. Reactions were carried out at +30° C. and were terminated by addition of 4.5 ml of 0.1 M $Na_2CO_3$, pH 11.2. The cells were then removed by centrifugation and the p-nitrophenol in the supernatant fluid was measured at 410 nm. One unit of enzyme activity is defined as the amount which hydrolyzes 1.0 nmol of substrate per minute under the conditions described above.

Culture media

The minimal medium media contained 0.67% of YNB medium (Difco) and 2% of sugar solidified with 2% agar. When regenerating protoplasts 1M sorbitol was added. As a rich basic medium YP medium, (1% Bacto yeast extract, 2% bacto peptone) was used. Strains, able or unable to ferment melibiose, were separated with fermentation indicator medium. Because of the pH change the melibiose fermenting strains will change the indicator color to yellow. This medium consisted of 1% Bacto-yeast extract, 2% Bacto-peptone, 2% melibiose, 2% Bacto-agar and 8 ml/l of 0.4% brom cresol purple solution. X-α-gal was used on plates in a following way: X-α-gal was dissolved in N'N'-dimethylformamide (20 mg/ml) and 0.1 ml of this solution was spread on agar plates (e.g. YPD, YP+galactose, YNB+melibiose).

The above mentioned plasmid and yeast strain constructions have been made by using the MEL1 gene of *Saccharomyces cerevisiae var. uvarum*. It will be understood that the use of the *Saccharomyces MEL1* gene is by way of example only. Use of the MEL1 gene as a DNA probe has shown that a family of MEL genes exists within the genus Saccharomyces. The other MEL genes can be differentiated on the basis of differences in DNA sequence, as revealed by restriction enzyme digestion and Southern hybridization (Tubb, R., Liljeström, P., Torkkeli, T. & Korhola, M. (1986) 13th International Conference on Yeast Genetics and Molecular Biology, Banff, Alberta, Canada 1986, Yeast 2 (Spec. Iss.) 1986 S396). Therefore it is feasible to consider use of a MEL gene cloned from other Saccharomyces strains, from other yeasts or from any organism able to produce a suitable α-galactosidase. The means to obtain expression of heterologous genes in yeast will be evident to those skilled in the art of recombinant DNA technology.

We claim:

1. A method for constructing an industrially used wild-type baker's, distiller's or brewer's yeast of the species *Saccharomyces cerevisiae* which expresses an α-galactosidase gene which has been transferred into said yeast by recombinant DNA techniques, wherein said method comprises the steps of:
    (a) isolating a gene encoding α-galactosidase;
    (b) operatively linking said gene into a plasmid;
    (c) transforming an industrially used wild-type baker's, distiller's or brewer's yeast of the species *Saccharomyces cerevisiae* with said plasmid or that part of aid plasmid which comprises said operatively linked gene;
    (d) selecting a transformed baker's, distiller's or brewer's yeast of step (c) which expresses said operatively linked gene wherein said selection is carried out by
        (i) direct selection of Mel+ transformants on a medium containing melibiose as the sole carbon source; or
        (ii) production of a blue-green color on a medium containing the chromogenic substrate X-α-gal.

2. A plasmid, wherein said plasmid is selected from the group consisting of plasmids pALK2, pALK4, pALK12, pALK20, pALK22, pALK23 and pALK52.

3. The method according to claim 1, wherein said gene is the MEL1 gene from *Saccharomyces cerevisiae* var. uvarum.

4. The method according to claim 1, wherein said plasmid containing said gene encoding α-galactosidase comprises all or part of one or more plasmids selected from the group consisting of plasmids pALK2, pALK4, pALK12, pALK20, pALK22, pALK23 and pALK52 and wherein said part of one or more plasmids comprises said gene encoding α-galactosidase.

5. The method according to claim 1, wherein the transformed yeast strain does not produce invertase.

6. The method according to claim 1 wherein the transformed yeast strain is MK270.

7. The method according to claim 1 wherein the transformed yeast strain is NCYC 1245.

8. The method according to claim 1, wherein said yeast strain is selected from the group consisting of M12E-2, M20E-1, N12E-1, pALK4/MK270 and pALK52/MK270.

9. The method according any of to 7 claims 3 to 8 or 1 wherein stable yeast strains are selected by using melibiose as the sole carbon source.

10. The method according to 7 any of claims 3 to 8 on 1, wherein stable yeast strains are selected by using X-α-gal substrate in the selection or screening medium.

11. An industrially used wild-type baker's, distiller's or brewer's yeast strain of the species *Saccharomyces cerevisiae*, which comprises a gene encoding α-galactosidase wherein said gene has been transformed into said yeast and said yeast constructed according to the method of claim 1, wherein said gene is present on a plasmid capable of autonomously replicating in said yeast or wherein said gene is integrated into a chromosome of said yeast by homologous recombination, and wherein said yeast strain is able to produce said α-galactosidase.

12. The yeast strain according to claim 11, wherein said gene encoding α-galactosidase is the MEL1 gene from *Saccharomyces cerevisiae* var. uvarum.

13. The yeast strain according to claim 11, wherein said plasmid comprises all or part of one or more plasmids selected from the group consisting of plasmids pALK2, pALK4, pALK12, pALK20, pALK22, pALK23 and pALK52 and wherein said part of one or more plasmids comprises said gene encoding α-galactosidase.

14. The yeast strain according to any of claims 11 to 13, which does not produce invertase.

15. The yeast strain according to any of claims 11 to 13, wherein the wild-type baker's distiller's or brewer's yeast strain is MK270.

16. The yeast strain according to any of claims 11 to 13, wherein the transformed wild-type baker's distiller's or brewer's yeast strain is NCYC 1245.

17. The yeast strain according to any of claims 11 to 13, wherein said yeast strain is selected from the group consisting of M12E-2, M20E-2, N12E-1, pALK4/MK270 and pALK52/MK270.

18. A method for constructing a plasmid for expressing α-galactosidase in an industrially used wild-type baker's, distiller's or brewer's yeast, which comprises:
    (a) isolating a gene encoding α-galactosidase from a yeast strain which expresses said gene; and
    (b) operatively-linking said gene into a plasmid wherein said plasmid is able to transform industrially used baker's, distiller's or brewer's wild-type yeast cells that are capable of expressing said gene encoding α-galactosidase and wherein plasmid is able to be stably maintained in said industrially used wild-type baker's, distiller's or brewer's yeast cells without auxotropic selection.

19. The method according to claim 18, wherein said gene is MEL1 from the species *Saccharomyces cerevisiae* var. uvarum.

20. The method according to claims 18 or 19, wherein said plasmid comprises all or part of one or more plasmids selected from the group consisting of plasmids pALK4, pALK12, pALK20, pALK22, pALK23 and pALK52 and wherein said part of one or more plasmids comprises said gene encoding α-galactosidase.

21. A method for utilization of raffinose or higher α-galactosides by an industrially used wild-type baker's, distiller's or brewer's yeast, said method comprising growing on industrially used wild-type baker's, distiller's or brewer's yeast strain in medium containing raffinose or higher α-galactosides wherein said yeast strain expresses a gene encoding α-galactosidase which has been transferred into said yeast strain by the method of claim 1, and wherein said utilization results in hydrolysis of an α-galactosidic bond in said raffinose or higher α-galactoside by said gene.

22. The method according to claim 21 wherein said gene is MEL1 from *Saccharomyces cerevisiae* var. uvarum.

23. The method according to claim 21, wherein said yeast strain comprises all or part of one or more plasmids selected from the group consisting of plasmids pALK2, pALK4, pALK12, pALK20, pALK22, pALK23 and pALK52 and wherein said part of one or more plasmids comprises aid gene encoding α-galactosidase.

24. The method according to claims any of 21 to 23, wherein the said yeast strain is MK270.

25. The method according to any of claims 21 to 23, wherein said yeast strain is selected from the group consisting of M12E-2, M20E-1, pALK4/MK270 and pALK52/MK270.

26. A method for producing α-galactosidase using an industrially used wild-type baker's, distiller's or brewer's yeast strain from the species *Saccharomyces cerevisiae*, said method comprising:
(a) transferring a gene encoding α-galactosidase into an industrially used wild-type baker's, distiller's or brewer's yeast strain according to the method of claim 1, wherein said gene is maintained in said yeast strain as part of an autonomously replicating plasmid or integrated into a chromosome of said yeast strain by homologous recombination:
(b) growing said yeast strain from part (a) under conditions which allow expression of said gene; and
(c) purifying and recovering said α-galactosidase.

27. The method according to claim 26, wherein said gene is MEL1 from the species *Saccharomyces cerevisiae* var. uvarum.

28. The method according to claim 26, wherein said yeast strain comprises all or part of one or more plasmids selected from the group consisting of plasmids pALK4, pALK12, pALK20, pALK22, pALK23 and pALK52 and wherein said part of one or more plasmids comprises said gene encoding α-galactosidase.

29. The method according to any of claims 26 to 28, wherein the said yeast strain does not produce invertase.

30. The method according to any of claims 26 to 28, wherein the said yeast strain is MK270.

31. The method according to any of claims 26 to 28, wherein said yeast strain is selected from the group consisting of M12E-2, M20E-1, pALK4/MK270 and pALK52/MK270.

32. A method for the transformation of an industrially-used wild-type baker's, distiller's or brewer's yeast with a gene that encodes an identification marker wherein said identification marker is α-galactosidase and wherein said method comprises transforming said yeast with a gene encoding said α-galactosidase according to the method of claim 1 such that said gene encoding said α-galactosidase integrates into the chromosome of said yeast in a manner which permits detection of said gene and identification of said yeast following restriction digestion of said chromosome.

33. The method according to claim 32, wherein said gene is MEL1 from the species *Saccharomyces cerevisiae* var. uvarum.

* * * * *

UNITED STATES PATENT AND TRADEMARK OFFICE
CERTIFICATE OF CORRECTION

PATENT NO. : 5,055,401
DATED : October 8, 1991
INVENTOR(S) : Liljestrom et al.

It is certified that error appears in the above-indentified patent and that said Letters Patent is hereby corrected as shown below:

On the title page, item [57], Abstract, line 3, delete "+".
On the title page, change "33 Claims, 10 Drawing Sheets" to read --33 Claims, 11 Drawing Sheets--.
In the drawings, Sheet 4 of the figures should be labeled --FIG. 4--.
The sheet of drawing consisting of Figure 10, should be added as Sheet 11, as shown on the attached page.

UNITED STATES PATENT AND TRADEMARK OFFICE
CERTIFICATE OF CORRECTION

PATENT NO. : 5,055,401

DATED : October 8, 1991

INVENTOR(S) : Liljestrom et al.

It is certified that error appears in the above-indentified patent and that said Letters Patent is hereby corrected as shown below:

In column 1, in line 8, delete "(E.C.1.2.1.22)" and replace therein -- (E.C. 3.2.1.22);
in line 29, after the word "Background", insert the word -- Art --.

In column 3, in line 34 delete "LFU2" and replace therein -- LEU2 --;
in line 58, delete "x-α-galactosidase" and replace therein -- X-α-galactoside --;

In column 4, in line 28, delete "meribiose" and replace therein -- melibiose --;
in line 33, delete "n-Galactosidase" and replace therein -- α-Galactosidase--;
in line 37, delete "sucrose" and replace therein -- raffinose --.

In column 6, in line 10, insert the word -- the -- between the word "containing" and "2.8";
in line 32, delete the period after "(1982)" and replace therein a comma;
in line 67, delete "PALK11" and replace therein -- pALK11 --;
in line 68, delete "BamH1" and replace therein -- BamHI --.

UNITED STATES PATENT AND TRADEMARK OFFICE
CERTIFICATE OF CORRECTION

PATENT NO. : 5,055,401

DATED : October 8, 1991

INVENTOR(S) : Liljestrom et al.

It is certified that error appears in the above-indentified patent and that said Letters Patent is hereby corrected as shown below:

In column 8, in line 64, delete "MEL+" and replace therein -- Mel+ --.

In column 9, delete the last two lines.

In column 10, in line 28, insert the word --while-- between "α-galactosidase" and "M12E-2";

in line 42, delete "$5=10^3 U$" and replace therein -- $5 \times 10^3 U$ --;

in line 56, delete "$7.8-10^5$" and replace therein -- $7.8 \cdot 10^5$ --.

In column 11, in lines 39-40, delete "MEL1 5' region" and replace therein -- MEL1 region --;

in line 42, insert a parenthesis before "1986)";

in line 48, delete "PALK22" and replace therein -- pALK22 --.

In column 12, in line 36, delete "Na2CO$_3$" and replace therein -- Na$_2$CO$_3$ --;

in line 44, delete "media";

in line 46, delete "IM" and replace therein -- 1 M --;

in line 47, insert "was used" between "medium" and "YP".

UNITED STATES PATENT AND TRADEMARK OFFICE
CERTIFICATE OF CORRECTION

PATENT NO. : 5,055,401
DATED : October 8, 1991
INVENTOR(S) : Liljestrom et al.

It is certified that error appears in the above-indentified patent and that said Letters Patent is hereby corrected as shown below:

In column 13, line 57 of claim 9, insert --to-- after "according" and after "of" delete "to 7";
line 60 of claim 10, delete "to 7";
line 60 of claim 10, delete "on" and replace there --or--.
In column 14, in line 10 of claim 18, insert --said--;
line 37, before "plasmid";
line 53 of claim 21, delete "on" and replace therein --an--.
In column 15, in line 1, delete "aid" and replace therein --said--;
in line 3 of claim 24, delete "claims any of" and replace therin --any of claims--.

Signed and Sealed this

Ninth Day of August, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,055,401
DATED : October 8, 1991
INVENTOR(S) : LILJESTRÖM et al.

It is certified that error appears in the above-indentified patent and that said Letters Patent is hereby corrected as shown below:

On the title page, please insert --[30] foreign application priority data: April 11, 1986 [FI] Finland . . . 861548--.

Signed and Sealed this

Sixth Day of December, 1994

Attest:

BRUCE LEHMAN

Attesting Officer     Commissioner of Patents and Trademarks